United States Patent [19]

Bowlin et al.

[11] Patent Number: 5,714,359
[45] Date of Patent: Feb. 3, 1998

[54] APPARATUS AND METHOD FOR ELECTROSTATIC ENDOTHELIAL CELL SEEDING IN A VASCULAR PROSTHESIS

[75] Inventors: Gary L. Bowlin, Akron; Stanley E. Rittgers, Hudson, both of Ohio

[73] Assignee: The University of Akron, Akron, Ohio

[21] Appl. No.: 541,248

[22] Filed: Oct. 12, 1995

[51] Int. Cl.$^6$ .......................... C12N 11/00; C12N 13/00; C12N 11/02; C12N 5/00
[52] U.S. Cl. ...................... 435/174; 204/403; 435/173.1; 435/177; 435/180; 435/283.1; 435/395; 623/11
[58] Field of Search ...................... 435/174, 177, 435/180, 173.1, 240.23, 283.1, 285.2, 395; 600/36; 623/11; 204/403

[56] References Cited

U.S. PATENT DOCUMENTS

| | | | |
|---|---|---|---|
| 4,939,151 | 7/1990 | Bacehowski et al. | 435/284 |
| 5,037,378 | 8/1991 | Muller et al. | 600/36 |
| 5,256,141 | 10/1993 | Gencheff et al. | 604/53 |

*Primary Examiner*—David M. Naff
*Attorney, Agent, or Firm*—Renner, Kenner, Greive, Bobak, Taylor & Weber

[57] ABSTRACT

An apparatus and method are provided for in vitro seeding of endothelial cells onto a surface such as a luminal wall of a vascular prosthesis. The apparatus contains an internal conductor and an external conductor, and a support means which maintains a suspension of endothelial cells in contact with the surface and which maintains the surface between the internal and external conductors while altering the charge on the surface. The internal conductor is an insulated wire and the external conductor has a bore through which the internal conductor passes. A vascular prosthesis containing a suspension of endothelial cells sealed within its lumen fits within the bore of the external conductor and the internal conductor wire passes through the lumen. While the prosthesis is rotated, an electrical potential is applied between the internal and external conductors altering the surface charge of the luminal wall of the prosthesis to facilitate adhesion of endothelial cells to the luminal wall.

19 Claims, 5 Drawing Sheets

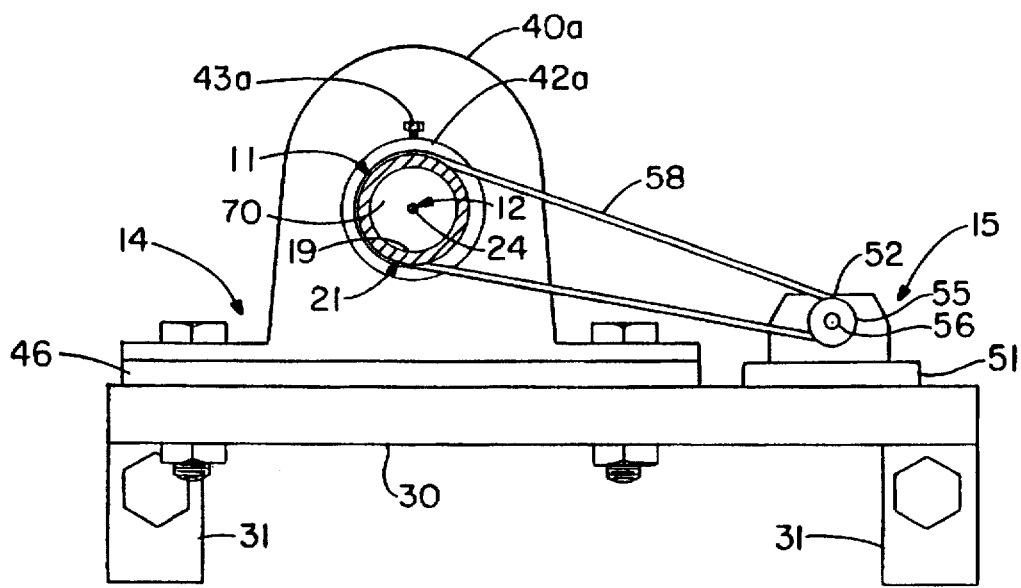
FIG.-6
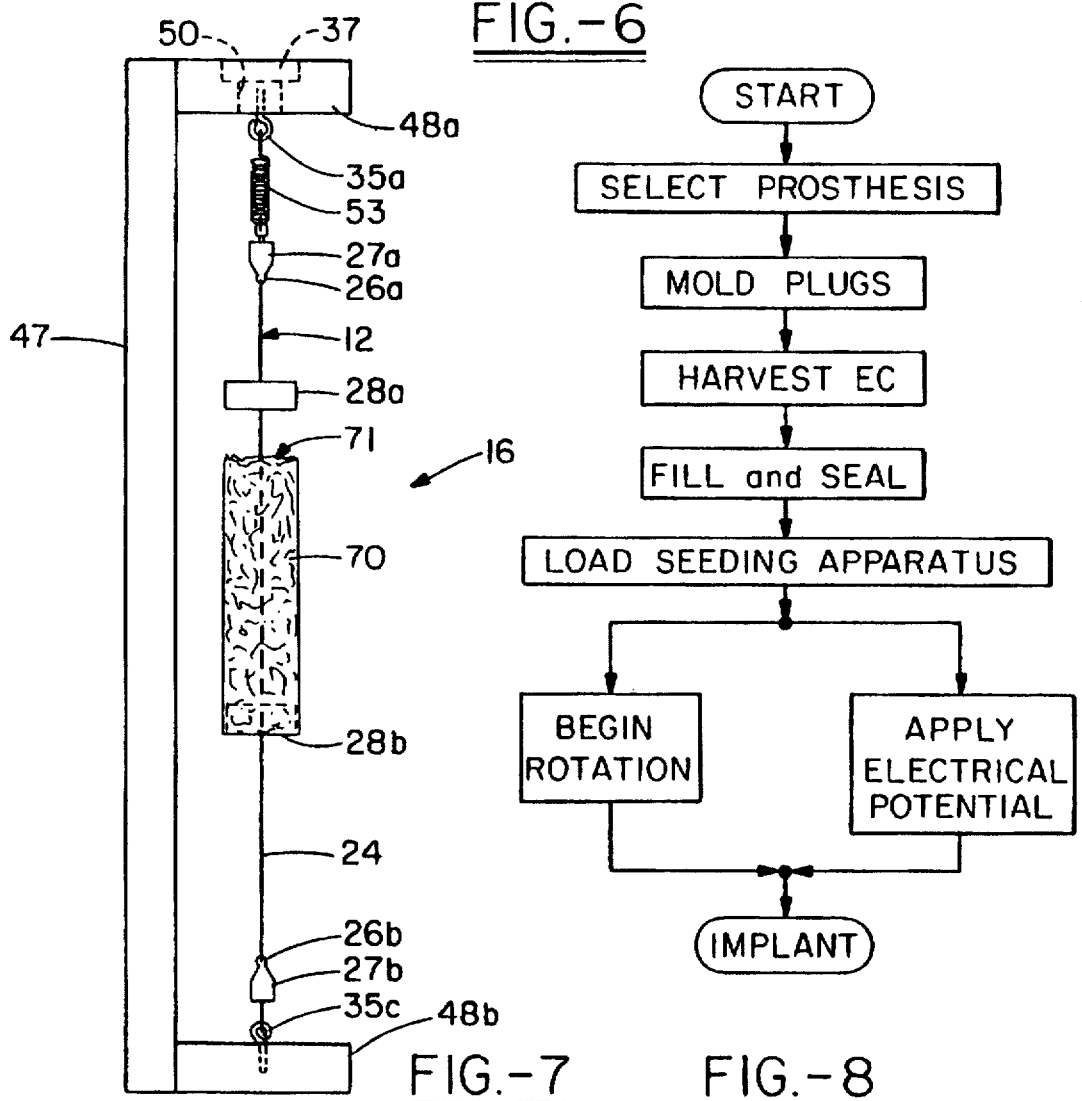
FIG.-7
FIG.-8

APPARATUS AND METHOD FOR ELECTROSTATIC ENDOTHELIAL CELL SEEDING IN A VASCULAR PROSTHESIS

TECHNICAL FIELD

The invention herein relates to methods and devices designed to facilitate the attachment of cells to a surface. More particularly, the invention relates to such methods and devices for the seeding of endothelial cells on the luminal wall of small diameter vascular prostheses. Specifically, the invention relates to a method and apparatus for enhancing endothelial cell adhesion to the luminal surface by temporarily altering the surface charge to a more positive state.

BACKGROUND ART

Heretofore it has been known to use synthetic prostheses in surgical operations for the repair of diseased or damaged, small diameter (<6 mm) blood vessels in humans. A major problem with use of synthetic small diameter vascular prostheses is poor long-term patency. The endothelial cell (EC) seeding of these vascular prostheses has led to an increased patency in humans and has led to complete healing in lab animals. The reason for high failure rates of small diameter vascular prostheses is due to the formation of acute, spontaneous thrombosis and chronic intimal hyperplasia. The thrombosis is initiated by platelets reacting with any non-endothelialized, foreign surface to initiate a platelet plug. This plug then acts as a template for the blood coagulation proteins. Over time, this platelet plug continues to grow resulting in occlusion, or failure, of the small diameter vascular graft. Thus, there is a recognized need for a better EC seeding technique of vascular prostheses to provide long-term patency and eventual healing.

Under normal circumstances, platelets circulate through the vascular system in a non-adherent state. This non-adherence is accomplished by the endothelial cells lining the vascular system. The EC have several factors which contribute to their non-thrombogenic mechanism. These are the negative surface charge, the heparin sulfate in their glycocalyx, the production and release of prostacylin, adenosine diphosphate, endothelium-derived relaxing factor, and thrombomodulin. Knowing this about EC, attempts have been undertaken to "disguise" artificial grafts by seeding autologous EC onto the graft prior to implantation. Research has shown that the adherence of more EC to the graft during the seeding process leads to enhanced healing times and reduced failure rates.

Chronic failure of the synthetic vascular grafts is due to intimal hyperplasia which principally occurs at the anastomosis. The exact cause leading to intimal hyperplasia has not been evident in research so as to explain the long-term failure of vascular prostheses. Intimal hyperplasia can apparently be initiated by many factors, including native vessel-prosthetic compliance mismatch and EC denudation due to increased shear stresses or mechanical damage which promotes the EC to synthesize growth factors to initiate smooth muscle cell (SMC) proliferation.

Intimal thickening is created by a combination of cellular proliferation and extracellular matrix accumulation. Myofibroblasts generate fibrous cells within the media to lead to intimal thickening of the adjacent native vessel. The SMC proliferation from the native vessel to the prosthetic vessel intima also contributes, to intimal hyperplasia. This SMC proliferation seems to be initiated and controlled by the EC present. Studies have shown that SMC proliferation occurs only underneath EC and does not occur where EC are absent. The proliferation slows down as EC repair progresses, except in the anastomotic region.

A number of EC seeding techniques have been used. One of these is a single-staged technique using a four step preclotting technique. The other techniques are: forcible injection, static adhesion seeding-preclotting, vacuum cell seeding, and subendothelial extracellular matrix seeding.

The single-staged technique for EC seeding is conducted during the preclotting of the graft. The preclotting process is designed to take full advantage of the reaction of thrombin and fibrinogen to preclot the graft. The first step of the process is to form thrombin. This is accomplished by injecting autologous blood into the graft lumen. Clotting of the blood in the graft indicates the presence of thrombin. Also during this time, fibrin is forming in the graft interstices.

The graft is then injected with unheparinized autologous blood to expose the graft for several seconds. Excess blood is wiped from the outside of the graft with a sponge. Then another portion of unheparinized, autologous blood is injected into the graft lumen to expose the graft for several more seconds. The outside of the graft is again wiped with a sponge to remove any excess blood. The objective of these last two steps is to utilize thrombin generated in the first step to form fibrin and seal the graft interstices.

The final step is to place the graft in heparin and inflate the graft with heparinized autologous blood repeatedly until hemostasis has been achieved. In this step, the open end of the graft is clamped with a non-crushing clamp. The objectives of this final step are to seal completely the graft interstices and to neutralize all the thrombin within the graft. The neutralization of the thrombin is done by a reaction with heparin. This neutralization is necessary because the thrombogenicity of the vascular grafts has been attributed to residual thrombin. The EC seeding during this preclotting technique is accomplished by placing harvested autologous EC into the first three aliquots of blood used in the process.

In the static adhesion seeding-preclotting technique the harvested EC are resuspended in an appropriate suspending medium, such as a saline solution, or blood plasma, and placed within the graft lumen. Both ends of the graft are clamped. The filled graft is then placed horizontally and periodically rotated over a period of several minutes. The unadhered cells are rinsed away by a gentle rinse with a saline solution. The graft is then ready for implantation.

In the forcible injection seeding-preclotting technique harvested EC are resuspended in Hank's solution. This suspension is divided into several aliquots of heparinized autologous blood. This blood-EC mixture is then injected forcibly with a plastic syringe into the graft. Both ends of the graft are clamped. These preclotting-seeding injections continue until hemostasis occurs. One problem with this type of preclotting along with the static adhesion preclotting techniques is that they are not adequate for fully heparinized patients. Another problem with these techniques is that after preclotting the surface may be rough and thrombogenic. These are two major limitations of the preclotting-seeding techniques described above.

The vacuum cell EC seeding technique was developed to induce a rapid EC coverage on the vascular prosthesis prior to implantation. This technique uses a special chamber in which a graft is placed. The graft is clamped at one end and the other end attached to a syringe filled with a washing medium and a syringe filled with an EC suspension. A vacuum is then applied to the system and the washing medium pulled through the graft. After pressure equilibrium, the cell suspension is pulled through the graft. One of the prerequisites of this method is to have a microporous graft. This method leads to an evenly distributed EC layer on the graft lumen. One benefit of this technique is that the total EC seeding time is significantly reduced. One limitation of this technique is that the EC at this point were mainly in the spheroid adhesion phase with the flattening of the adhered EC occurring over a two hour incubation period.

The subendothelial extracellular matrix seeding technique begins by coating the graft lumen with a uniform, naturally produced subendothelial extracellular matrix. This extracellular matrix (ECM) leads to a more suitable vascular prosthesis lumen for EC adhesion, growth, and differentiation when compared to grafts coated with fibronectin or basement membrane. An advantage of this technique is that it contains adhesive glycoproteins, proteoglycans (heparin sulfate), and EC growth factors. The limitation of this technique is the amount of culture time required. The first culture period is required to produce the ECM on the graft lumen. The other culture period is for the EC seeding process required to produce a lumen which resembles a native vessel.

Previous platelet adhesion experiments have verified that platelet adhesion can be controlled by the platelet-surface interaction potential energy. This potential energy is due to the interaction of the two surface charges and their complimentary surface potentials, or total double layer potentials. This double layer potential is developed by ions within the suspending medium interacting with the surface charges. EC experiments have also indicated a charge interaction in the adhesion process.

Platelet experiments have shown that the adhesion process is affected by temporarily altering the surface charge. If the surface charge is made more negative, the platelet adhesion process is inhibited. The spreading also seems to be slowed under these conditions. When the surface charge is temporarily made more positive, the platelet adhesion process is enhanced. Likewise, the spreading is also enhanced under a more positive surface charge.

Experiments conducted on EC adhesion on varying surface charges show similar results to those obtained for platelets. The EC adhesion process was reduced with an increasingly negative surface charge. The increasingly positive surface charge led to an enhanced EC adhesion. The main problem with these experiments is that the surface charges are a function of the material and permanent.

The other similarity among these experiments is the actual adhesion process once the cells are in contact with a surface. Once the cells settle to the surface, the platelets, as well as the EC, then initiate adhesion by extending pseudopods. The central portion of the cell then follows these pseudopods to flatten and adhere to the surface. This portion of the adhesion process resembles "webbing" which connects the pseudopods. Under normal circumstances, the adhesion and spreading process for EC takes anywhere from several minutes to several hours depending on the surface conditions.

As previously discussed, altering the surface charge can increase or decrease the spreading time. Increased spreading of the seeded EC is an important aspect of the process. Studies have shown that EC adherence to vascular graft material under flow conditions is dependent on the EC-surface interaction and the time allowed for adhesion and spreading prior to the initial exposure to shear stress. This is because EC exposed to fluid shear stresses that are not washed away when implanted are tightly adhered or fully spread. As many as 70% of the EC are removed from implanted EC seeded grafts over the first several minutes with 3.7%/hr lost over the period from 30 minutes to 24 hours using the forcible injection EC seeding technique.

The morphology of the adhered EC on the graft surface after the proposed procedure will be circular and flattened. It is assumed that the circular, flattened EC will change morphology to a more elongated, flattened shape upon initial exposure to the implanted shear stresses. Many studies have shown that EC will realign parallel to the direction of flow in response to local shear stresses.

Studies have also concluded, by scanning and transmission electron microscopy, that the surface free energy determines the number of contact sites between the graft and the flattened fibroblasts. A high surface free energy promotes cell adhesion, spreading, and contact sites. A low surface free energy inhibits cell adhesion, spreading, and contact sites. Also large contact regions, adhesion sites, between surfaces and fibroblast cells can be obtained on less negatively charged surfaces. It has further been shown that increasing the surface negativity leads to decreased contact regions, thus, showing the importance of the cell-surface electrostatic interaction in the cell adhesion process.

Accordingly, it is most desirable to obtain an apparatus and method for the electrostatic seeding of endothelial cells on a non-thrombogenic graft surface without making the graft surface thrombogenic.

DISCLOSURE OF THE INVENTION

In light of the foregoing, it is an object of the invention to provide an endothelial cell (EC) seeding technique and apparatus to enhance the EC adhesion during seeding, prior to implantation of small diameter (<6 mm) synthetic vascular prostheses.

Another object of the invention is the provision of such an EC seeding technique and apparatus which uses electrostatic forces with gravitational forces to enhance endothelial cell adhesion and maturation.

A further object of the invention is the provision of such an EC seeding technique and apparatus which provides enhanced endothelial cell adhesion onto a graft surface which is nonthrombogenic without making it thrombogenic.

Yet another object of the invention is the provision of such an EC seeding technique and apparatus which takes non-thrombogenic surfaces and temporarily makes them more positive to cause them to be more attractive to the endothelial cells during seeding and after seeding flows the graft material to revert back to its natural negative surface charge which is non-thrombogenic.

Still a further object of the invention is the provision of such an EC seeding technique and apparatus which prevents thrombosis which would occlude a small diameter graft and also allows healing of any non-endothelialized areas resulting in increased long term patency of the prosthesis.

The foregoing and other objects of the invention which will become apparent as the detailed description proceeds are achieved by an apparatus for the seeding of cells on a surface comprising: conductor means for temporarily altering the electrical charge on the surface to be seeded; and, support means for maintaining a solution containing cells in contact with the surface to be seeded while the charge on the surface is temporarily altered by said conductor means.

Other objects of the invention are attained by an apparatus for seeding endothelial cells on the luminal wall of a vascular prosthesis, the apparatus comprising: an external conductor having a bore extending the length thereof; an internal conductor including a length of electrically conductive wire having at least one elastomeric plug member molded thereon, said wire and said at least one plug member being disposed within said bore of said external conductor and said at least one plug member being adapted to sealingly engage the vascular prosthesis to be seeded; a support assembly having a base portion, at least one support block extending from said base portion, at least one bearing mount mounted on said base portion, and at least one bearing adapted to rotatably journal said external conductor within said at least one bearing mount; a drive assembly for selectively rotating the prosthesis, said drive assembly having a motor, and a drive belt connected to said motor and in driving communication with the prosthesis; and, a voltage source for applying an electrical potential between said external and internal conductors; whereby the vascular prosthesis filled with endothelial cell solution is sealingly mounted on said plug of said internal conductor and is maintained in a spaced relationship from said internal conductor within said bore of said external conductor and said voltage source applies an electrical potential between said external conductor while said drive assembly rotates the prosthesis, thereby temporarily altering the surface charge of the prosthesis to facilitate adhesion of endothelial cells thereto.

Still other objects of the invention are achieved by a method for seeding endothelial cells on the luminal wall of a vascular prosthesis, comprising the steps of: passing an internal conductor wire through the lumen of the vascular prosthesis; sealing one end of the prosthesis around the internal conductor wire; filling the prosthesis with a solution of suspended endothelial cells; sealing the other end of the prosthesis; placing the internal conductor and prosthesis into the bore of an external conductor; rotating the prosthesis; and, applying temporarily an electrical potential between the internal and external conductors while the prosthesis is being rotated.

DESCRIPTION OF THE DRAWINGS

For a complete understanding of the objects, techniques and structure of the invention reference should be made to the following detailed description and accompanying drawings wherein:

FIG. 6 is a cross-sectional view of the apparatus of FIG. 4, taken along the line 6—6;

FIG. 7 is an elevational side view of the filling apparatus according to the invention; and, FIG. 8 is a flow diagram depicting the steps of the method according to the invention.

BEST MODE FOR CARRYING OUT THE INVENTION

With the foregoing background in mind, experiments were conducted on human umbilical vein endothelial cells (HUVEC), using a parallel plate capacitor, to determine the effects of altering the surface charge of flattened polytetrafluoroethylene (PTFE) graft material with regard to HUVEC adhesion. After the HUVEC were cultured and harvested a cell count was performed to determine the number of HUVEC/ml. The experiments were accomplished by placing a static pool of HUVEC suspended in Dulbecco's Phosphate Buffered Saline (DPBS) solution in a Teflon® (Teflon is a Registered Trademark of E. I. du Pont de Nemours & Co.) ring held in position on the flattened PTFE graft.

Three experiments were performed on the HUVEC. The first was the control experiment to determine the mount and quality of EC adhesion on a graft having a non-induced surface charge for comparison of EC morphology. This experiment was conducted both with and without antioxidants.

The second experiment was to determine the mount and quality of EC adhesion on the graft when placed between the plates of the capacitor while an electrical potential was applied thereto.

The third experiment was like the second, but included an antioxidant in the HUVEC-DPBS solution.

Because EC tend to be more active when in the non-confluent state and less active in the confluent state, each of the experiments was performed using both confluent and non-confluent HUVEC. Contact interaction leads to proliferation inhibition and membrane stability. The non-confluent case (very little contact between EC) leads to an active EC state during proliferation. Thus, the presence of an antioxidant in experiments one and three was to protect the EC membrane.

Experiments two and three were conducted using applied voltages of 0.75 V and 1.50 V.

The number of HUVEC in the spheroid, discoid, and flattened state was then determined for each of the experiments and compared to determine the effect of applied voltage, confluent v. non-confluent state, and effect of antioxidants.

The results obtained confirmed that endothelial cell adhesion and spreading on PTFE is affected by the surface charge. The results further indicate that increasing the magnitude of induced positive charge on the PTFE material increases: (1) the total number of HUVEC adhered; (2) the total and percentage of HUVEC adhered in the flattened phase; and, (3) the total HUVEC adhered in the discoid phase.

Figure 1:
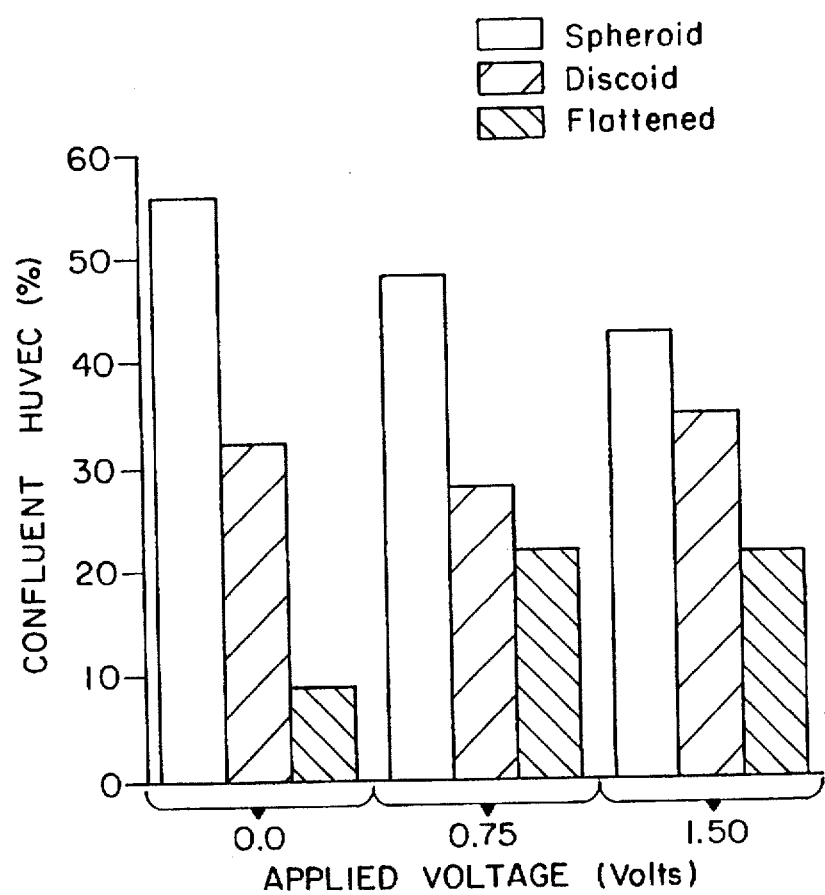
FIG. 1 is a graphic depiction of the results of parallel plate capacitor adhesion experiments where the resuspending solution contained antioxidants.
Figure 2:
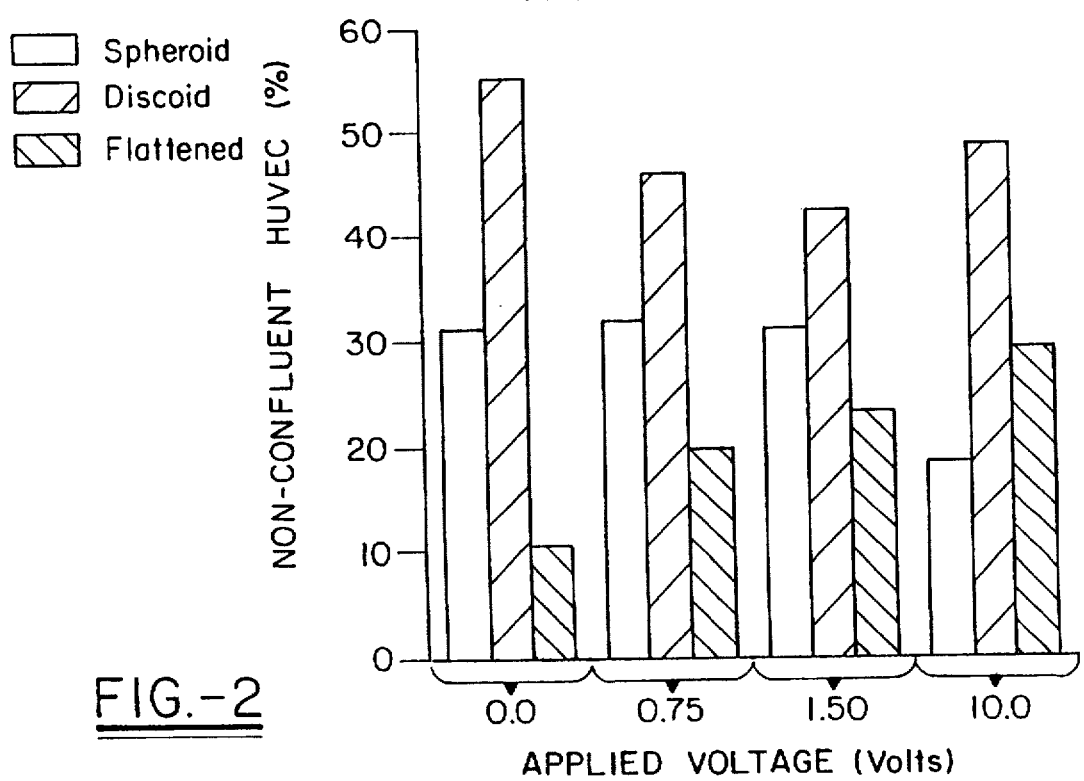
FIG. 2 is a graphic depiction similar to FIG. 1 where the resuspending solution contained no antioxidants.
Figure 3:
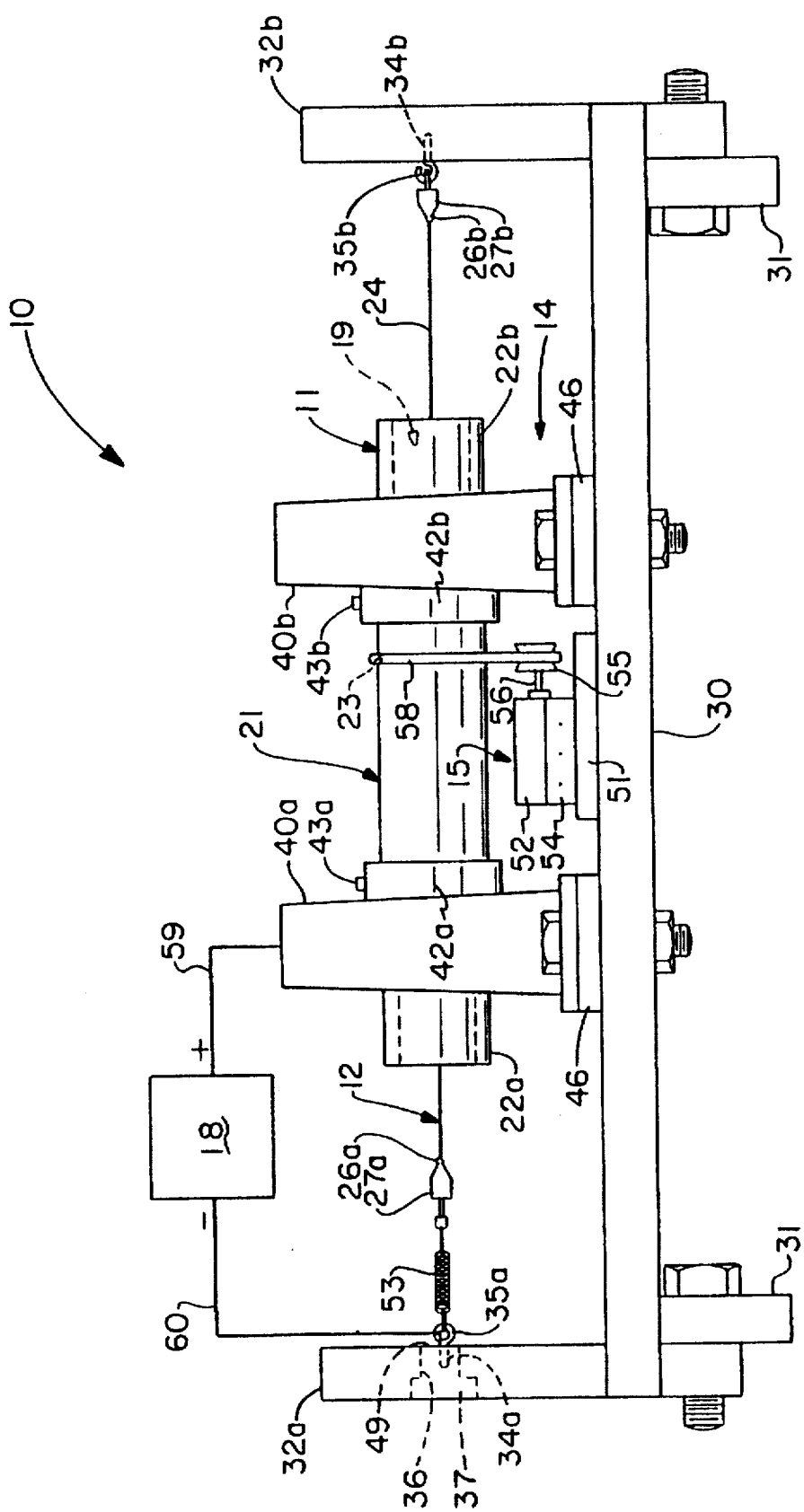
FIG. 3 is an elevational side view of the apparatus according to the invention.

The results also indicate a trend in the dam between confluent and non-confluent HUVEC. As is apparent from FIGS. 1 and 2, the percentage and total discoid HUVEC adhered is larger for the non-confluent, while the percentage and total spheroid HUVEC is higher for the confluent. However, no noticeable trend can be seen between the antioxidant and no-antioxidant experiments. Accordingly, the present invention was developed to take advantage of the experimental results discussed above for endothelial cell seeding of small diameter vascular prostheses.

Referring now to the drawings, and more particularly to FIGS. 3–6, it can be seen that an apparatus for electrostatic seeding of endothelial cells is designated generally by the numeral 10. The apparatus 10 is comprised generally of an external conductor 11, an internal conductor 12, a support assembly 14, a drive mechanism 15, a filling apparatus 16, and a voltage source 18.

The external conductor 11 is a hollow cylindrical member having a concentric internal bore 19. The external conductor 11 is preferably fabricated from a round length of an appropriate machinable metal such as 303 stainless steel. It is desirable that the conductor 11 be coated with an appropriate conductive polymer or, alternatively, fabricated entirely from such a conductive polymer, to prevent heavy metal contamination of the graft. The conductor 11 includes a pair of set screw grooves 20a and 20b in its outer surface 21, proximal to ends 22a and 22b, respectively, thereof. Similarly, a drive groove 23 is located in the surface 21 of the conductor 11, approximately midway between the grooves 20.

Figure 5:
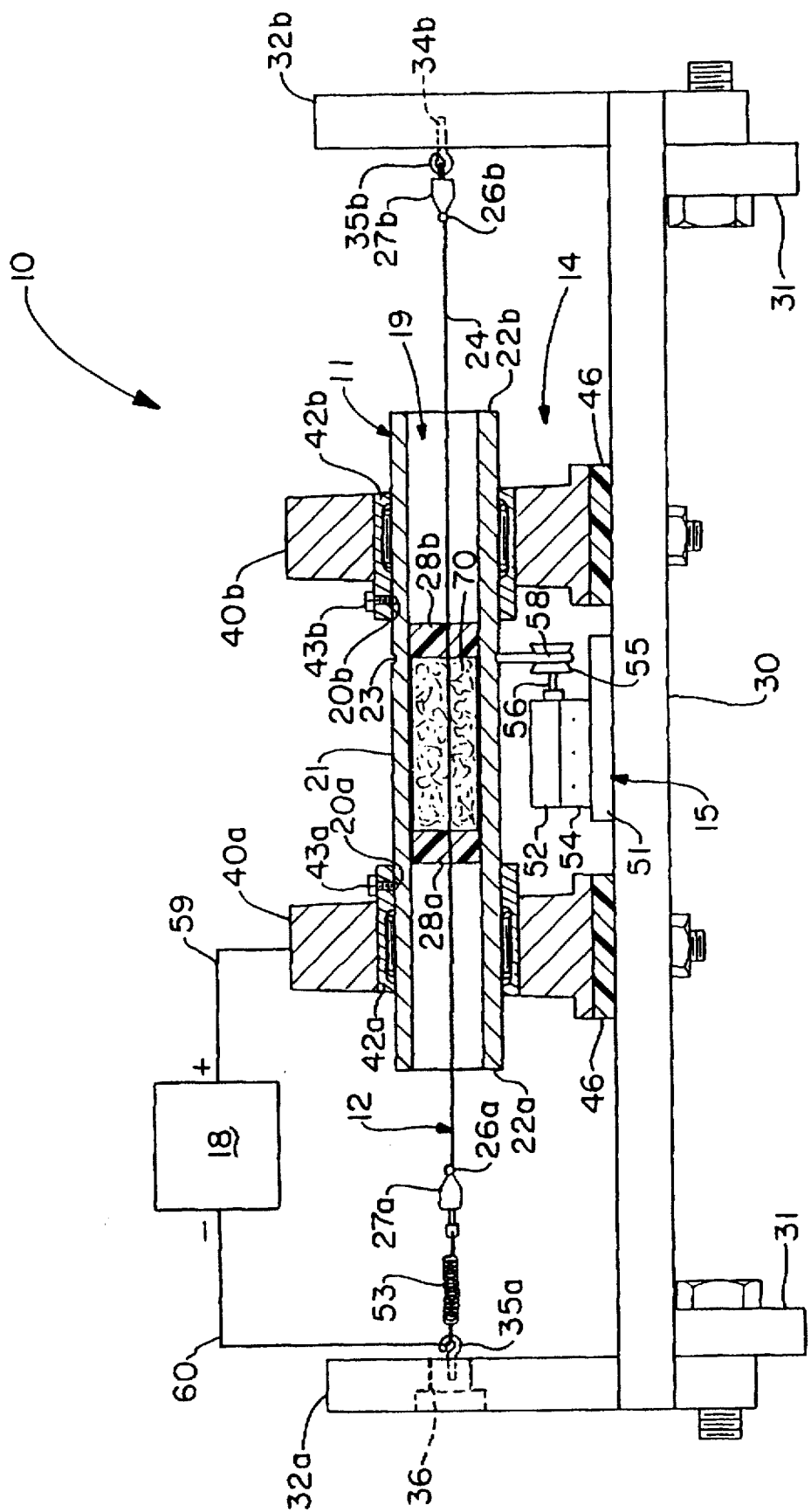
FIG. 5 is a cross-sectional view of the apparatus of FIG. 4 taken along the line 5—5.

With particular reference to FIG. 5 it can be seen that the internal conductor 12 is comprised of a strand of electrically conductive wire 24, preferably AWG-32 silver-plated copper, coated with a conductive polymer such as is commercially available under the trademark GORE-TEX® (GORE-TEX is a Registered Trademark of W. L. Gore & Associates Inc.) or other appropriate material. The ends 26 of the wire 24 are each secured to an end terminal 27. The end terminals 27 are ball bearing swivels preferably of a nickel-plated steel. The conductor 12 further includes a pair of spaced silicon rubber plugs 28 which are molded directly on the wire 24. For reasons which will become apparent as the description continues the plugs 28 have an outside diameter approximating the inside diameter of the graft to be seeded. Similarly, the plugs 28 are spaced apart from one another along the wire 24 at a distance which is slightly less than the length of the graft to be seeded. Those skilled in the art will recognize that the plugs 28 may be molded from a commercially available resilient silicon compound such as is commercially available under the trademark Sylgard® (Sylgard is a Registered Trademark of Dow Corning Corp.) using sectional molds made an appropriate non-stick material, such as is commercially available under the trademark Teflon®.

Referring again to FIGS. 3 and 4, the support assembly 14 comprises a base plate portion 30 having legs 31 affixed thereto. A pair of end supports 32 are disposed at opposite ends of the base plate 30. The end supports 32 are blocks fabricated preferably of an appropriate non-conductive polymer. The end support 32b includes a threaded aperture 34 substantially centered in the support 32b for the receipt of a screw eye 35b. The second support 32a similarly includes a somewhat larger plug receiving aperture 36 substantially centered therein, directly opposite the screw eye 35b. As shown, the end supports 32 are mounted to the base plate 30 by way of notches 38 in the sides 39 of the base plate 30. A support plug 37 is adapted to be received in the plug receiving aperture 36. The support plug 37 is fabricated from an appropriate material such as was used for the end supports 32, and includes a generally cylindrical head portion 41 and a reduced diameter body 45. A threaded aperture 34b is provided in the end face 49 of the plug 37 for the receipt of a screw eye 35a. It should thus be recognized that the diameter of the body portion 41 of the plug 37 is slightly smaller than the diameter of the plug receiving aperture 36 of the end support 32a. As shown a coil spring tensioner 53 is fitted on the screw eye 35a.

The support assembly 14 further includes a pair of bearing mounts or pillow blocks 40 for rotatably journaling the external conductor 11. Accordingly, the external conductor 11 is fitted within a pair of bearings 42 and secured thereto by tightening set screws 43 in the bearing locking collars 44 so as to engage the set screw grooves 20 in the outer surface 21 of the conductor 11. The bearings 42 are mounted in the pillow blocks 40, which are, in turn, mounted on the base plate 30. A non-conductive gasket 46 is interposed between the pillow blocks 40 and the base plate 30 to insulate electrically the pillow blocks 40 from the base 30. It should be noted that the bore 19 of the external conductor 11 is axially aligned with the apertures 34 and 36 of the end supports 32a and 32b respectively. As depicted in FIG. 7, the filling apparatus 16 is comprised of a support section 47 having a pair of end sections 48 disposed at each end thereof. The end section 48a includes a bore 50 to accommodate the support plug 37 previously described with respect to the support assembly 14, while the end section 48b is provided with a screw eye 35c. As shown, the end sections 48 are disposed at opposite ends of the support section 47 such that the plug receiving bore 50 is axially aligned with the screw eye 35c.

Figure 4:
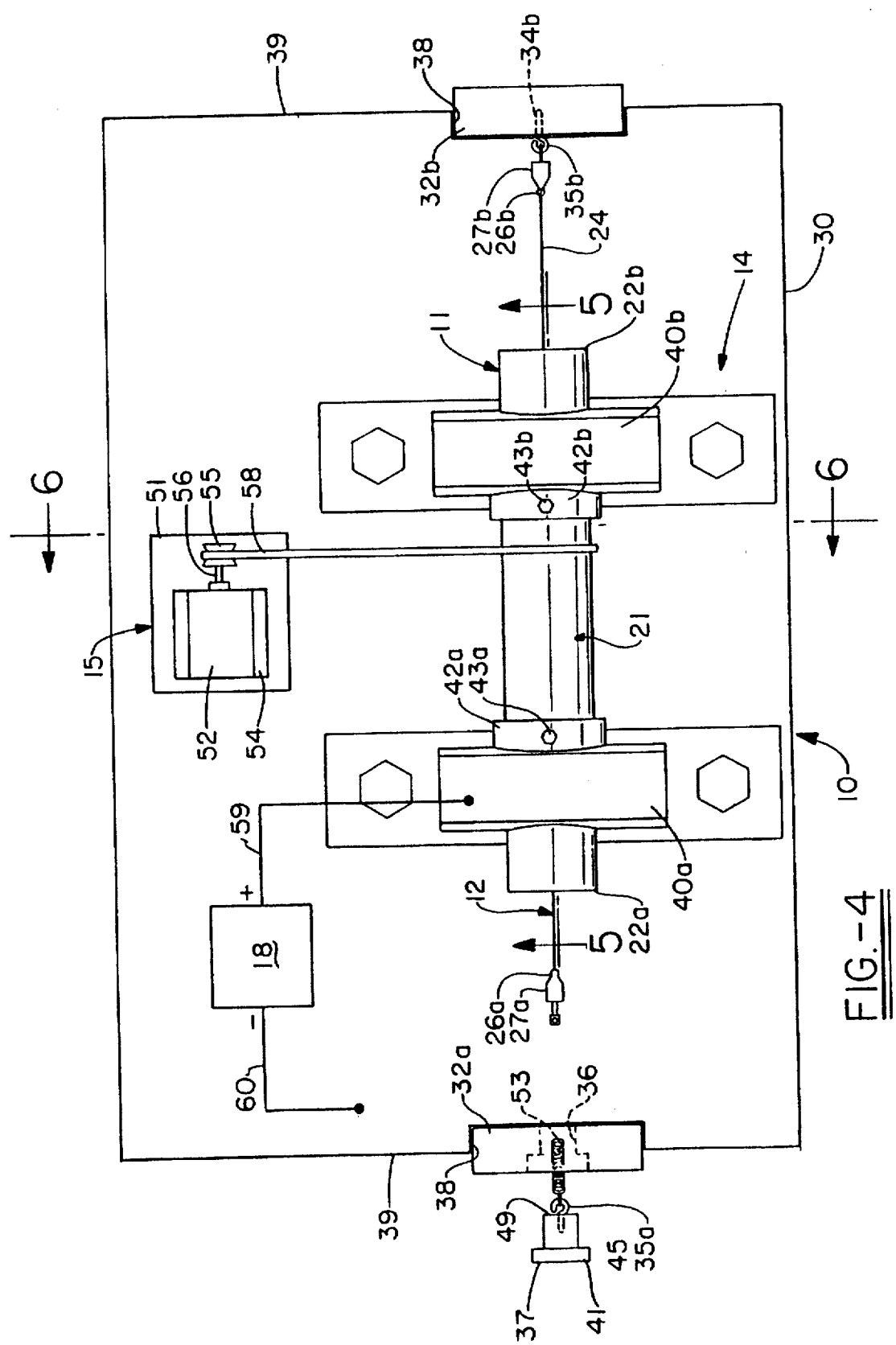
FIG. 4 is a top plan view of the apparatus of FIG. 3.

With reference now to FIGS. 4 and 6, the drive mechanism 15 includes a motor support base 51 which is affixed to the base plate portion 30 of the support assembly 14. A motor 52 is mounted to the motor support base 51 by way of a mounting bracket 54. The motor 52 is preferably a synchronous AC motor operating at 115 V/60 Hz and capable of running at approximately 1/12 RPM in a clockwise rotation. A drive sheave 55 is mounted on the motor shaft 56. The sheave 55 may be made of a reinforced nylon or other appropriate material. A drive belt 58 is fitted in the drive groove 23 of the external conductor 11 and drivingly engages the sheave 55.

The voltage source 18 may be a conventional multi-range voltage calibrator capable of generating a 0-20 V output with an accuracy of ±0.05% of the full scale reading. The positive lead 59 is electrically connected to the external conductor 11 by way of the pillow block 40, while the negative lead 60 is connected to the internal conductor 12 by way of the screw eye 35. Accordingly, an electrical potential is applied across the apparatus.

In operation a synthetic small diameter vascular prosthesis 70 to be seeded with autologous EC is fitted on the internal conductor 12 by passing an end 26b of the wire 24 through the lumen of the graft 70. The graft 70 is positioned over the plugs 28 and secured to the conductor 12 by seating the graft 70 on the lower plug 28b using 2-O silk suture or the like. This creates a seal between the graft 70 and the plug 28b to prevent fluid leakage during the seeding process. The ends 26 of the wire 24 are then affixed to the screw eye 35c and spring 53 respectively of the end section 48b and support plug 37. The support plug 37 is, in turn, mounted in the end section 48a of the filling apparatus 16 such that the open end 71 of the graft 70 is facing upwardly. The graft 70 may then be slowly filled with the EC-Saline solution to the point of overflow so as to eliminate air in the graft 70. Once the graft 70 is filled, the open end 71 is then secured to the upper plug 28a using silk suture in a similar manner as was done for the lower plug 28b.

After the graft 70 has been filled and closed the internal conductor 12 is removed from the filling apparatus 16 and transferred to the support assembly 14. The internal conductor 12 is fitted within the external conductor 11 by passing an end 26 of the wire 24 through the bore 19 using a lead wire (not shown). The end terminals 27 of the internal conductor 12 are then secured to the end supports 32 as shown.

Seeding of EC in the graft 70 is thus accomplished by energizing the motor 52 so as to initiate rotation of the external conductor 11 which, in turn, causes rotation of the graft 70 and internal conductor 12. This rotation is desirable to prevent uneven distribution of EC due to gravitational forces. Simultaneously, an electrical potential is applied across the apparatus 10 by the voltage source 18. Those skilled in the art will recognize that the internal and external conductors act as plates of a capacitor while the graft material acts as a dielectric interposed therebetween. As such, the surface charge of the graft lumen is temporarily altered to a more positive state so as to provide a more suitable environment for EC adhesion. After the seeding procedure is completed, and the electrical potential removed, the surface charge of the graft returns to its original, more negative, non-thrombogenic state. The graft may then be removed from the internal conductor by removing the silk suture. The graft is ready for implantation after being gently rinsed to remove the excess EC-Saline solution.

While the method of the present invention should now be apparent in view of the foregoing discussion of the operation of the apparatus, the preferred method will now be discussed briefly with reference to FIG. 8. The first step involves the selecting of a synthetic vascular prosthesis of an appropriate size and quality for the implant procedure. Next plugs of an appropriate size to fit within the prosthesis are molded on the internal conductor. Autologous endothelial cells are harvested and suspended in a suspension medium. The internal conductor is fitted to the prosthesis by passing the internal conductor through the lumen thereof, and sealing one end of the prosthesis to one of the molded plugs. The internal conductor, carrying the prosthesis is then suspended upright in the filling apparatus by connecting the end terminals thereof to the screw eye of the first end section and the spring of the support plug respectively. With the prosthesis suspended upright it may be filled to overflow with the suspended endothelial cell solution. Once the prosthesis is filled, the open end thereof may be sealed to the remaining molded plug.

After the filled prosthesis is sealed it is removed from the filling apparatus and transferred to the seeding apparatus by disconnecting the end terminal from the screw eye of the first end section and removing the support plug from the second end section. The prosthesis and internal conductor are mounted in the seeding apparatus by passing the disconnected end terminal through the bore of the external conductor and pulling the prosthesis into the bore. The disconnected end terminal is then connected to the screw eye of the first support block while the support plug is fitted to the aperture of the second support block. With the internal conductor and prosthesis mounted in the seeding apparatus rotation of the external conductor is initiated by energizing the motor. Simultaneously, an electrical potential is applied across the conductors by energizing the voltage source. As such, the surface charge of the luminal wall of the prosthesis is temporarily altered to a more positive state allowing the endothelial cells to adhere thereto in greater numbers as well as in a more flattened state.

Thus, it can be seen that the objects of the invention have been satisfied by the structure presented above. While in accordance with the patent statutes only the best mode and preferred embodiment has been presented and described in detail, it is to be understood that the invention is not limited thereto or thereby. Accordingly, for an appreciation of the true scope and breadth of the invention reference should be made to the following claims.

What is claimed is:

1. An apparatus for the in vitro seeding of endothelial cells on an entire surface of a vascular prosthesis comprising:

conductor means for temporarily altering the electrical charge on the entire surface to be seeded by providing an internal conductor without openings and an external conductor spaced apart from said internal conductor; and, support means for maintaining a solution containing endothelial cells in contact with the entire surface to be seeded, wherein said support means maintains the entire surface to be seeded between said internal conductor and said external conductor while the charge on the entire surface is temporarily altered by said conductor means.

2. The apparatus according to claim 1, wherein said conductor means further comprises a voltage source for applying an electrical potential between said internal and external conductors and through the entire surface of the vascular prosthesis.

3. The apparatus according to claim 2, wherein said internal conductor comprises a continuous length of electrically conductive wire through which none of the solution can flow.

4. The apparatus according to claim 2, wherein said external conductor is a length of electrically conductive material having a bore running the entire length thereof.

5. The apparatus according to claim 4, wherein said internal conductor is disposed within said bore of said external conductor and maintained at an equally spaced predetermined distance therebetween.

6. The apparatus according to claim 3, wherein said support means comprises at least one mounting member engaging said internal conductor, said at least one mounting member being adapted to maintain the surface to be seeded in spaced relation to said internal conductor.

7. The apparatus according to claim 5, wherein the surface to be seeded is held in sealing engagement with said at least one mounting member.

8. The apparatus according to claim 6, wherein said at least one mounting member is a flexible plug molded on said wire.

9. The apparatus according to claim 2, wherein said conductor means further comprises drive means for rotating the surface to be seeded.

10. The apparatus according to claim 2, wherein said conductor means further comprises a support assembly having journal means for rotatably supporting said external conductor.

11. The apparatus according to claim 9, wherein said support assembly includes means for holding and tensioning said internal conductor within said bore of said external conductor.

12. The apparatus according to claim 8, wherein said drive means comprises a motor and a drive belt drivingly connected to said motor and to said external conductor.

13. An apparatus for in vitro seeding endothelial cells on substantially all of the luminal wall of a vascular prosthesis, the apparatus comprising:

an external conductor having a bore extending the length thereof;

an internal conductor including a length of electrically conductive insulated wire, said wire being centrally disposed within said bore of said external conductor and said wire being adapted to sealingly engage the vascular prosthesis to be seeded;

a support assembly having a base portion, at least one support block extending from said base portion, at least one bearing mount mounted on said base portion, and at least one bearing adapted to rotatably journal said external conductor within said at least one bearing mount;

a drive assembly for selectively rotating the vascular prosthesis to be seeded, said drive assembly having a motor, and a drive belt connected to said motor and in driving communication with the vascular prosthesis and, a voltage source for applying an electrical potential between said external and internal conductors and through substantially all of the luminal wall, wherein the luminal wall functions as a dielectric material;

whereby the vascular prosthesis filled with endothelial cell solution is sealingly mounted on said internal conductor and is maintained in an equally spaced apart relationship from said internal conductor within said bore of said external conductor and said voltage source applies an electrical potential across said conductors while said drive assembly continuously rotates the vascular prosthesis, thereby temporarily altering the surface charge of the vascular prosthesis to a more positive state to facilitate adhesion of endothelial cells to substantially all of the luminal wall and whereupon removal of said voltage source causes the vascular prosthesis to return to a non-thrombogenic state.

14. The apparatus according to claim 13, further comprising a filling assembly for supporting said internal conductor and the prosthesis to be seeded while the prosthesis is filled and sealed, the filing assembly having a base portion, and a pair of support blocks extending from said base portion, said internal conductor being suspended between said support blocks while the prosthesis is filled and sealed.

15. The apparatus according to claim 13, wherein said internal conductor has at least one elastomeric plug member molded thereon, said at least one elastomeric plug member having a diameter corresponding to the internal diameter of the prosthesis to be seeded.

16. A method for in vitro seeding endothelial cells on the entire luminal wall of a vascular prosthesis, comprising the steps of:

passing an internal conductor insulated wire without openings through the lumen of the vascular prosthesis;

sealing one end of the prosthesis around the internal conductor wire;

filling the prosthesis with a solution of suspended endothelial cells;

sealing the other end of the prosthesis;

placing the internal conductor and prosthesis into the bore of an external conductor;

continuously rotating the prosthesis; and, applying temporarily an electrical potential between the internal and external conductors and through the luminal wall while the prosthesis is being continuously rotated such that the surface charge of the entire luminal wall is temporarily altered to facilitate adhesion of endothelial cells to the entire luminal wall.

17. The method according to claim 16, comprising the further steps of molding at least one plug member on the internal conductor wire prior to the passing of the internal conductor wire through the lumen of the prosthesis, the diameter of the plug member corresponding to the inside diameter of the vascular prosthesis.

18. The method according to claim 17, wherein the steps of sealing the prosthesis are accomplished by sealing the ends of the prosthesis to the plug member.

19. The method according to claim 16, comprising the further step of suspending the internal conductor wire and prosthesis between a pair of support block while the internal conductor wire and prosthesis are inside the bore of the external conductor.

* * * * *